United States Patent [19]

Yamada et al.

[11] 4,368,198
[45] Jan. 11, 1983

[54] CEPHALOSPORINS

[75] Inventors: Hirotada Yamada; Takenari Nakagome, both of Nishinomiya; Toshiaki Komatsu, Takarazuka, all of Japan

[73] Assignee: Sumitomo Chemical Company Limited, Osaka, Japan

[21] Appl. No.: 18,212

[22] Filed: Mar. 7, 1979

Related U.S. Application Data

[62] Division of Ser. No. 773,729, Mar. 2, 1977, Pat. No. 4,165,373.

[30] Foreign Application Priority Data

Mar. 3, 1976 [JP] Japan .................................. 51-23482
Mar. 3, 1976 [JP] Japan .................................. 51-23483
Mar. 3, 1976 [JP] Japan .................................. 51-23484
Mar. 3, 1976 [JP] Japan .................................. 51-23485

[51] Int. Cl.³ ................. C07D 501/20; A61K 31/545
[52] U.S. Cl. ...................................... 424/246; 544/22; 544/27
[58] Field of Search .................. 544/16, 22, 21, 26, 544/27, 28; 424/246

[56] References Cited

U.S. PATENT DOCUMENTS 3,966,717  6/1976  Cook et al. ............................ 544/22
3,974,153  8/1976  Cook et al. ............................ 544/22
4,061,861  12/1977  Lunn et al. ............................ 544/26
4,138,554  2/1979  Naito et al. ............................ 544/22
4,297,488  10/1981  Christen et al. ....................... 544/22

Primary Examiner—Nicholas S. Rizzo
Attorney, Agent, or Firm—Sughrue, Mion, Zinn, Macpeak & Seas

[57] ABSTRACT

A compound of the formula (I):

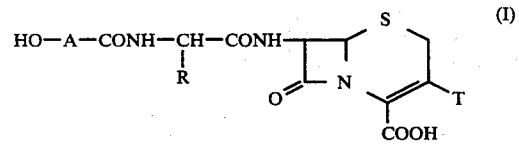

wherein
A is a monocyclic or polycyclic heteroaromatic ring containing at least one nitrogen atom as a hetero atom, which may be unsubstituted or substituted with one or more substituents;

R is a phenyl group which can be unsubstituted or substituted or a thienyl group;

T is (1) a —CH$_2$—S—Het group, where Het is a tetrazolopyridazine ring, a triazolopyridazine ring, or a triazolopyridine ring, (2) a

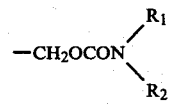

group wherein R$_1$ and R$_2$, which may be the same or different, each is a hydrogen atom or a (C$_1$–C$_4$)alkyl group, (3) a —CH$_2$N$_3$ group or (4) is —CH$_2$S—D group in which D is a group selected from the group consisting of

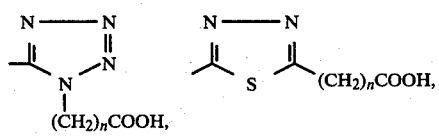

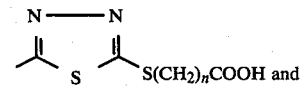

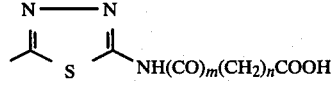

where m and n each is 0 to 3: with the proviso that
(a) when the HO—A— moiety is a

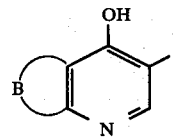

group where B represents the non-metallic atoms necessary to complete a pyridine ring, a pyrimidine ring or a pyrazole ring, each of which may be unsubstituted or substituted, then T is the —CH$_2$SD group wherein D is as defined above, and
(b) when T is the —CH$_2$N$_3$ group, then R is a substituted phenyl group and the non-toxic, pharmaceutically acceptable salts thereof, processes for preparing the same, and antimicrobial compositions containing the same.

25 Claims, No Drawings

CEPHALOSPORINS

This is a division of application Ser. No. 773,729, filed Mar. 2, 1977 now U.S. Pat. No. 4,165,373.

BACKGROUND OF THE INVENTION

1. Field of the Invention

This invention relates to novel cephalosporin compounds. More particularly, this invention relates to cephalosporin compounds useful as chemotherapeutic agents and particularly having Pseudomonas activity in addition to a broad antimicrobial spectral activity.

2. Description of the Prior Art

It is known that cephalosporin series compounds such as Cephalothin and Cefazolin are very effective and are widely used as chemotherapeutic agents for infectious diseases caused by Gram-positive or Gram-negative bacteria.

However, these cephalosporin series compounds have no effect on infectious diseases caused by *Pseudomonas aeruginosa* which have been increasingly spreading in recent years, and are often very difficult to cure. Cephalosporin series compounds which are effective against *Pseudomonas aeruginosa* are not yet commercially available.

SUMMARY OF THE INVENTION

As the result of various studies seeking a cephalosporin series compound having a strong anti-Pseudomonas activity and a broad antimicrobial spectral activity, it has been found that cephalosporins of the formula (I) as described below and the pharmaceutically acceptable salts thereof have a strong antimicrobial activity against Gram-positive as well as Gram-negative bacteria including *Pseudomonas aeruginosa* and are useful as antimicrobial agents for the treatment or the prevention of infectious diseases caused by Gram-negative or Gram-positive bacteria.

Particularly, the compounds of the invention exhibit a noticeable antimicrobial activity against bacteria to which known cephalosporin series compounds are barely effective, such as *Pseudomonas aeruginosa*, indole positive Proteus, Serratia, *Enterobacter aerogenus*, and Cephaloridine resistant *E. coli*.

Accordingly, an object of this invention is to provide novel cephalosporin compounds which are useful as antimicrobial agents.

In one embodiment, this invention provides cephalosporin compounds represented by the formula (I):

$$HO-A-CONH-\underset{R}{CH}-CONH-\left[\text{β-lactam}\right]-T \quad (I)$$
$$COOH$$

wherein A represents a monocyclic or polycyclic heteroaromatic ring containing at least one nitrogen atom as a hetero atom, which may be unsubstituted or substituted with one or more substituents; R represents a phenyl group, a substituted phenyl group or a thienyl group; T represents (1) a $-CH_2-S-Het$ group wherein Het represents a tetrazolopyridazine group, a triazolopyridazine group or a triazolopyridine group, (2) a $$-CH_2OCON\begin{matrix}R_1\\R_2\end{matrix}$$

group wherein $R_1$ and $R_2$, which may be the same or different, each represents a hydrogen atom or an alkyl group having 1 to 4 carbon atoms, (3) a $-CH_2N_3$ group or (4) a $-CH_2S-D-$ group in which D represents a group selected from the group consisting of

[triazole structure with $(CH_2)_n COOH$], [thiadiazole structure with $(CH_2)_n COOH$],

[thiadiazole structure with $S-(CH_2)_n COOH$], and

[thiadiazole structure with $NH(CO)_m(CH_2)_n COOH$]

wherein m and n each represents an integer of 0 to 3; with the proviso that (a) when the HO-A- moiety is a

[structure with OH, B, and N showing a fused bicyclic ring]

group wherein B represents the non-metallic atoms necessary to complete a pyridine ring, a pyrimidine ring or a pyrazole ring, each of which may be unsubstituted or substituted, then T is the $-CH_2SD$ group wherein D is as defined above, and (b) when T is the $-CH_2N_3$ group, then R is a substituted phenyl group and the non-toxic, pharmaceutically acceptable salts thereof.

In another embodiment of this invention, this invention provides processes for preparing the compounds of the formula (I) above.

In an even further embodiment of this invention, the invention provides an anti-microbial composition containing at least one compound of the formula (I) above.

DETAILED DESCRIPTION OF THE INVENTION

More specifically, the compounds of the present invention represented by the formula (I) include the following compounds having the formulae (I-a), (I-b), (I-c) and (I-d):

$$HO-A-CONH-\underset{R}{CH}-CONH-\left[\text{β-lactam}\right]-CH_2S-Het \quad (I-a)$$
$$COOH$$

and

-continued

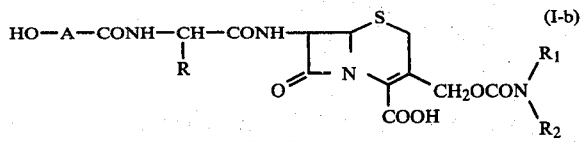

wherein A represents a monocyclic or polycyclic nitrogen-containing heteroaromatic group; R represents a phenyl group, a substituted phenyl group or a thienyl group; Het represents a tetrazolopyridazine group, a triazolopyridazine group or a triazolopyridine group and $R_1$ and $R_2$, which may be the same or different, each represents a hydrogen atom or an alkyl group having 1 to 4 carbon atoms;

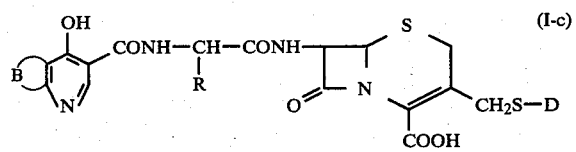

wherein R is as defined above; B represents the non-metallic atoms necessary to complete a pyridine ring, a pyrimidine ring or a pyrazole ring, each of which may be substituted or unsubstituted; and D represents

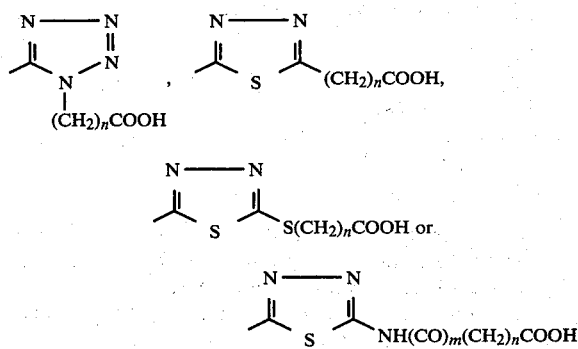

wherein n and m are as defined above; and

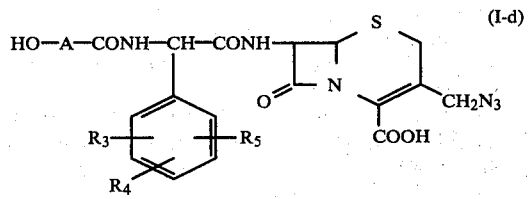

wherein A is as defined above; $R_3$ represents a hydroxy group, a protected hydroxy group, an amino group, a ureido group or a hydroxymethyl group; $R_4$ and $R_5$ each represents a member selected from the group consisting of a hydrogen atom, a nitro group, a dialkylamino group, an alkenoylamino group, an amino group, a hydroxy group, an alkanoyloxy group, a lower alkyl group, a lower alkoxy group, a halogen atom, a trifluoromethyl group, a hydroxymethyl group and a sulfamyl group.

In the above formulae (I), (I-a), (I-b) and (I-d), the heteroaromatic ring represented by A may be, for example, naphthyridine, pyrazolopyridine, pyridopyrazine, pyridopyrimidine, pyridine, pyrimidine, pyridazine and triazine. These heteroaromatic rings for A may be substituted with 1 to 4 substituents, of which examples are a halogen (e.g., fluorine, chlorine, bromine and iodine) atom, a lower alkyl group, a lower alkoxy group, a lower alkanoyl group, a lower alkoxycarbonyl group, a lower alkylthio group, a mercapto group, a hydroxy group, a lower alkoxymethyl group, a cyano group, a nitro group, a lower alkylsulfonyl group, an arylsulfonyl group, a sulfamoyl group, a carbamoyl group, an aryloxycarbonylamino group, an acetoacetylamino group, a lower alkylamino group, a lower dialkylamino group, a lower haloalkyl group, a lower alkenyl group, an aryl group, a cycloalkyl group, a cycloalkylene group, and a heterocyclic ring group containing 1 or 2 nitrogen atoms.

With respect to the above groups and the moieties contained therein as well as the groups and moieties to be described hereinafter, unless otherwise indicated, the term "lower alkyl" preferably includes an alkyl group or moiety having up to 4 carbon atoms; "lower alkoxy" preferably includes an alkoxy group or moiety having up to 4 carbon atoms; "lower alkanoyl" preferably includes an alkanoyl group or moiety having up to 5 carbon atoms; "lower alkoxycarbonyl" preferably includes an alkoxycarbonyl group or moiety having up to 5 carbon atoms; "lower alkylthio" preferably includes an alkylthio group or moiety having up to 4 carbon atoms; "lower alkoxymethyl" preferably includes an alkoxymethyl group or moiety having up to 5 carbon atoms; "lower alkylsulfonyl" preferably includes an alkylsulfonyl group or moiety having up to 4 carbon atoms; "arylsulfonyl" preferably includes a phenylsulfonyl group or moiety; "aryloxycarbonylamino" preferably includes a phenyloxycarbonylamino group or moiety; "lower alkylamino" preferably includes an alkylamino group or moiety having up to 4 carbon atoms; "lower dialkylamino" preferably includes a dialkylamino group or moiety of which each of the alkyl moieties thereof has up to 4 carbon atoms; "lower haloalkyl" preferably includes a chloro- or fluoro-substituted alkyl group or moiety having up to 4 carbon atoms, for example, chloromethyl, trifluoromethyl, 2,2,2-trichloroethyl; "lower alkenyl" preferably includes an alkenyl group or moiety having up to 4 carbon atoms; "aryl" preferably includes a phenyl group or moiety; "cycloalkyl" preferably includes a cycloalkyl group or moiety having 3 to 6 carbon atoms; "cycloalkylene" preferably includes a cycloalkylene group or moiety having 4 to 6 carbon atoms and "heterocyclic ring containing 1 or 2 nitrogen atoms" preferably includes pyrrolidinyl, morpholyl, piperazinyl or piperidinyl.

In the formula (I), the hydroxy group on the heteroaromatic ring A is preferably linked to a carbon atom adjacent the carbon atom to which the

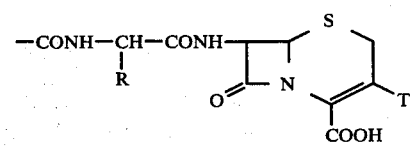

moiety is connected.

In the above formulae, R represents a phenyl group which may be unsubstituted or substituted or a thienyl group and the term "a phenyl group" which may be substituted as used with respect to R includes an optionally substituted phenyl group of the formula:

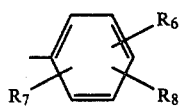

wherein $R_6$, $R_7$ and $R_8$, which may be the same or different, each represents a hydrogen atom, a nitro group, a lower dialkylamino (preferably, di-($C_1$-$C_4$)alkylamino) group, a lower alkanoylamino (preferably, ($C_2$-$C_5$)alkanoylamino) group, a lower alkylsulfonamido (preferably, ($C_1$-$C_4$)alkylsulfonamido) group, an amino group, a hydroxy group, a lower alkanoyloxy (preferably, ($C_2$-$C_5$)alkanoyloxy) group, a lower alkyl (preferably, ($C_1$-$C_4$)alkyl) group, a lower alkoxy (preferably, ($C_1$-$C_4$)alkoxy) group, a chlorine atom, a bromine atom, a fluorine atom, an iodine atom, a trifluoromethyl group, a hydroxymethyl group, or a sulfamyl group, preferably a hydrogen atom, a hydroxy group, a chlorine atom, a fluorine atom or a methoxy group.

The heterocyclic ring represented by the symbol Het in the —S—Het group may be unsubstituted or substituted with one to four of a ($C_1$-$C_4$)alkyl group, a ($C_1$-$C_4$)alkoxy group or a hydroxy group.

Examples of suitable groups for Het include tetrazolo[4,5-b]pyridazine-6-yl, 3-hydroxypyridazino[3,2-c]-s-triazol-6-yl, pyrido[2,1-c]-s-triazol-3-yl, s-triazolo[4,3-b]pyridazine-3-yl, s-triazolo[4,3-b]pyridazine-6-yl, 3-methyl-s-triazolo[4,3-b]pyridazine-6-yl and the like.

Further, $R_1$ and $R_2$ each represents a hydrogen atom or a lower alkyl group having 1 to 4 carbon atoms. Suitable examples of lower alkyl groups include a methyl group, an ethyl group, a propyl group, an n-butyl group, an isopropyl group, an isobutyl group and a t-butyl group.

The fused heterocyclic ring

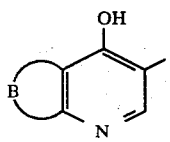

can contain one or more substituents such as a lower ($C_1$-$C_4$)alkyl group, a lower ($C_1$-$C_4$)alkoxy group, a lower ($C_2$-$C_5$)alkanoyl group, a lower ($C_2$-$C_4$)alkoxycarbonyl group, a lower ($C_1$-$C_4$)alkylthio group, a mercapto group, a hydroxy group, a lower ($C_1$-$C_4$)alkoxymethyl group, a halogen atom, a cyano group, a nitro group, a lower ($C_1$-$C_4$)alkylsulfonyl group, an arylsulfonyl group, a sulfamoyl group, a carbamoyl group, an aryloxycarbonylamino group, an acetoacetylamine, a lower ($C_1$-$C_4$)alkylamino group, a lower di-($C_1$-$C_4$)alkylamino group, a halo-($C_1$-$C_4$)alkyl group, an alkenyl group, an aryl group or a ($C_3$-$C_6$)cycloalkyl group.

Examples of suitble non-toxic pharmaceutically acceptable salts derived from the compounds of formula (I) include the sodium salt, the potassium salt, the calcium salt, the magnesium salt, the triethylamine salt, the diethanolamine salt, the morpholine salt, the procaine salt, the L-arginine salt, and the L-lysine salt.

The α-carbon atom of the side chain (phenylglycine moiety) attached to the 7-position of the formula (I) is an asymmetric carbon atom and therefore two optically active isomers exist. These two isomers (D-diastereomer and L-diastereomer) and the DL-form are included within the scope of the present invention, but the D-diastereomer is preferred.

Preferred examples of the compounds of this invention are as follows.

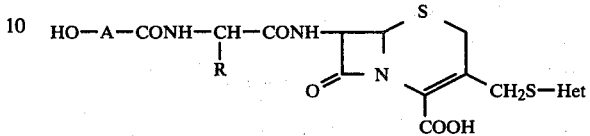

wherein A is a divalent heteroaromatic ring selected from the group consisting of a naphthyridine ring, a pyrazolopyridine ring, a pyridopyrazine ring, a pyridopyrimidine ring, a pyridine ring, and a pyridazine ring, each of which can be unsubstituted or substituted with a ($C_1$-$C_4$)alkylthio group; R is an unsubstituted group or a phenyl group substituted with one or more substituents selected from the group consisting of a hydroxy group, an amino group and a thienyl group; Het is a tetrazolopyridazine group, a triazolopyridazine group or a triazolopyridine group, each of which can be unsubstituted or substituted with a hydroxy group or a ($C_1$-$C_4$)alkyl group;

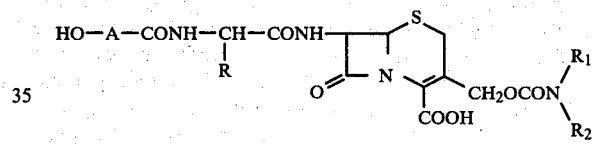

wherein A is a divalent heteroaromatic ring selected from the group consisting of a naphthyridine ring, a pyridopyrimidine ring and a pyridine ring, each of which can be unsubstituted or substituted with a ($C_1$-$C_4$)alkylthio group; R is a phenyl group which can be unsubstituted or substituted with one or two substituents selected from the group consisting of a hydroxy group, an amino group and a chloro atom; $R_1$ and $R_2$, which can be the same or different, each is a hydrogen atom or a ($C_1$-$C_4$)alkyl group;

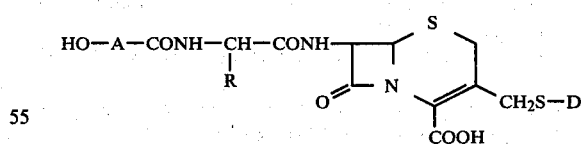

wherein A is a naphthyridine ring, a pyridopyrimidine ring or a pyrazolopyridine ring, each of which may be unsubstituted or substituted with a substituent selected from the group consisting of a ($C_1$-$C_4$)alkyl group or a ($C_1$-$C_4$)alkylthio group; R is a phenyl group which can be unsubstituted or substituted with one or more substituents selected from the group consisting of a hydroxy group, an amino group and a chlorine atom or a thienyl group; D is a group selected from the group consisting of groups of the formula

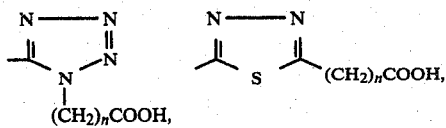

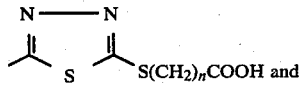

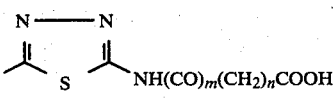

where m and n each is 0 to 3;

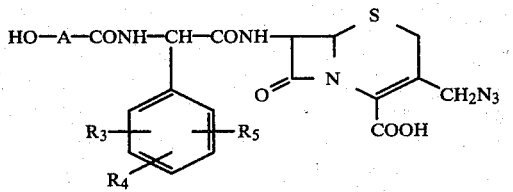

wherein A is a naphthyridine ring, a pyridine ring, a pyrimidine ring, a pyridazine ring or a triazine ring, each of which can be unsubstituted or substituted with a ($C_1$–$C_4$)alkoxy group or a hydroxy group; $R_3$ is a hydroxy group, a protected hydroxy group, an amino group, a ureido group or a hydroxymethyl group; $R_4$ and $R_5$, which can be the same or different, each is a hydrogen atom, a nitro group, a di-($C_1$–$C_4$)alkylamino group, a ($C_2$–$C_5$)alkanoylamino group, an amino group, a hydroxy group, a ($C_2$–$C_5$)alkanoyloxy group, a ($C_1$–$C_4$)alkyl group, a ($C_1$–$C_4$)alkoxy group, a halogen atom, a trifluoromethyl group, a hydroxymethyl group or a sulfamyl group.

Among these cephalosporins, the following compounds are preferred.

(1) 7-[D-α-(4-Hydroxy-1,5-naphthyridine-3-carboxamido)-α-(p-hydroxyphenyl)acetamido]-3-(tetrazolo[4,5-b]-pyridazine-6-ylthiomethyl)-3-cephem-4-carboxylic acid
and the non-toxic, pharmaceutically acceptable salts thereof (2) 7-[D-α-(4-Hydroxy-1,5-naphthyridine-3-carboxamido)-α-(p-hydroxyphenyl)acetamido]-3-(pyrido[2,1-c]-s-triazol-3-ylthiomethyl)-3-cephem-4-carboxylic acid
and the non-toxic, pharmaceutically acceptable salts thereof (3) 7-[D-α-(4-Hydroxypyridine-3-carboxamido)-α-(p-hydroxyphenyl)acetamido]-3-(tetrazolo[4,5-b]-pyridazine-6-ylthiomethyl)-3-cephem-4-carboxylic acid
and the non-toxic, pharmaceutically acceptable salts thereof (4) 7-[D-α-(4-Hydroxypyridine-3-carboxamido)-α-(p-hydroxyphenyl)acetamido]-3-carbamoyloxymethyl-3-cephem-4-carboxylic acid
and the non-toxic, pharmaceutically acceptable salts thereof (5) 7-[D-α-(4-Hydroxypyridine-3-carboxamido)-α-(m-aminophenyl)acetamido]-3-carbamoyloxymethyl-3-cephem-4-carboxylic acid
and the non-toxic, pharmaceutically acceptable salts thereof (6) 7-[D-α-(4-Hydroxypyridine-3-carboxamido)-α-phenylacetamido]-3-carbamoyloxymethyl-3-cephem-4-carboxylic acid
and the non-toxic, pharmaceutically acceptable salts thereof (7) 7-[D-α-(4-Hydroxy-1,5-naphthyridine-3-carboxamido)-α-(p-hydroxyphenyl)acetamido]-3-carbamoyloxymethyl-3-cephem-4-carboxylic acid
and the non-toxic, pharmaceutically acceptable salts thereof (8) 7-[D-α-(4-Hydroxy-1,5-naphthyridine-3-carboxamido)-α-phenylacetamido]-3-carbamoyloxymethyl-3-cephem-4-carboxylic acid
and the non-toxic, pharmaceutically acceptable salts thereof (9) 7-[D-α-(4-Hydroxy-1,5-naphthyridine-3-carboxamido-α-(m-aminophenyl)acetamido]-3-carbamoyloxymethyl-3-cephem-4-carboxylic acid
and the non-toxic, pharmaceutically acceptable salts thereof

(10) 7-[D-α-(2-Methylthio-5,8-dihydro-5-oxopyrido[2,3-d]-pyrimidine-6-carboxamido)-α-(p-hydroxyphenyl)acetamido]-3-carbamoyloxymethyl-3-cephem-4-carboxylic acid
and the non-toxic, pharmaceutically acceptable salts thereof

(11) 7-[D-α-(5,8-Dihydro-5H-8-oxopyrido[3,2-d]pyrimidine-7-carboxamido)-α-(p-hydroxyphenyl)acetamido]-3-carbamoyloxymethyl-3-cephem-4-carboxylic acid
and the non-toxic, pharmaceutically acceptable salts thereof

(12) 7-[D-α-(4-Hydroxy-1,5-naphthyridine-3-carboxamido-α-(3-chloro-4-hydroxyphenyl)acetamido]-3-carbamoyloxymethyl-3-cephem-4-carboxylic acid
and the non-toxic, pharmaceutically acceptable salts thereof

(13) 7-[D-α-(4-Hydroxy-1,5-naphthyridine-3-carboxamido-α-(p-hydroxyphenyl)acetamido]-3-(5-carboxymethyl-1,3,4-thiadiazol-2-ylthiomethyl)-3-cephem-4-carboxylic acid
and the non-toxic, pharmaceutically acceptable salts thereof

(14) 7-[D-α-(4-Hydroxy-1,5-naphthyridine-3-carboxamido-α-(p-hydroxyphenyl)acetamido]-3-(1-carboxymethyl-1,2,3,4-tetrazol-5-ylthiomethyl)-3-cephem-4-carboxylic acid
and the non-toxic, pharmaceutically acceptable salts thereof

(15) 7-[D-α-(4-Hydroxy-1,5-naphthyridine-3-carboxamido)-α-(p-hydroxyphenyl)acetamido]-3-azidomethyl-3-cephem-4-carboxylic acid
and the non-toxic, pharmaceutically acceptable salts thereof The compounds of the formula (I) of the present invention can be prepared by the following methods:

The compounds of the formula (I) above can be prepared by reacting a carboxylic acid of the formula (II):

HO—A—COOH     (II)

wherein A is as defined above, or a reactive derivative thereof, with a compound of the formula (III):

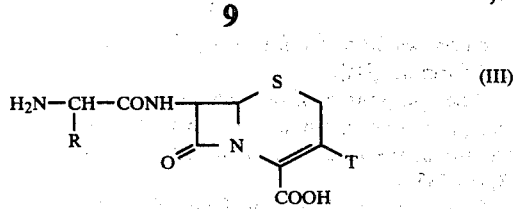

wherein R and T are as defined above, or a salt or derivative thereof.

Referring more particularly to this process, inert solvents which can be used in the reaction between the compounds of the formulae (II) and (III) include polar solvents such as dichloromethane, chloroform, acetone, tetrahydrofuran, dioxane, acetonitrile, methyl isobutyl ketone, ethyl alcohol, dimethylformamide, dimethylacetamide, dimethyl sulfoxide, nitromethane, hexamethylphosphoric triamide, sulfolane, and the like; non-polar solvents such as benzene, toluene, petroleum ether, n-hexane and the like; and a mixture thereof. These solvents can also be used in combination with water.

The reactive derivatives of the compound (II) mean reactive derivatives of a carboxyl group, for example, an acid halide, an acid anhydride, an acid azolide, an active ester, an acid azide and the like. Referring more particularly to these reactive derivatives, examples include mixed acid anhydrides or symmetric acid anhydrides with acids such as dialkyl phosphoric acids, phenyl phosphoric acid, diphenyl phosphoric acid, dibenzyl phosphoric acid, halogenated phosphoric acids, dialkyl phosphorous acids, sulfuric acid, methanesulfonic acid, toluenesulfonic acid, naphthalenesulfonic acid, alkylcarbonates, aliphatic carboxylic acids (for example, pivalic acid, pentanoic acid, isopentanoic acid, 2-ethylbutanoic acid); acid azolides with imidazole, substituted imidazoles, dimethylpyrazole, triazole, tetrazole, and the like; and active esters such as cyanomethyl ester, methoxymethyl ester, vinyl ester, propargyl ester, p-nitrophenyl ester, 2,4-dinitrophenyl ester, trichlorophenyl ester, pentachlorophenyl ester, methanesulfonylphenyl ester, phenylazophenyl ester, phenylthiophenyl ester, p-nitrophenylthio ester, p-cresolthio ester, carboxymethylthio ester, pyranyl ester, pyridyl ester, piperidyl ester, 8-quinolylthio ester, and esters with N,N'-dimethylhydroxylamine, 1-hydroxy-2-(1H)-pyridone, N-hydroxysuccinimide or N-hydroxyphthalimide.

Further, when the compounds of the formula (II) are used in the form of the free acid (or the salt thereof), it is preferred to carry out the reaction in the presence of coupling agents such as N,N'-dicyclohexylcarbodiimide, N-cyclohexyl-N-morpholinoethylcarbodiimide, N-cyclohexyl-N-(4-diethylaminocyclohexyl)carbodiimide, N,N'-diethylcarbodiimide, N,N'-diisopropylcarbodiimide, N-ethyl-N-(3-dimethylaminopropyl)carbodiimide, N,N'-carbonyldi(2-methylimidazole), pentamethyleneketene-N-cyclohexylimine, diphenylketene-N-cyclohexylimine, alkoxyacetylenes, 1-alkoxy-1-chloroethylenes, trialkyl phosphites, polyphosphoric acid ethyl ester, polyphosphoric acid isopropyl ester, phosphorus oxychloride, oxalylchloride, triphenylphosphine, diethylphosphonyl azide, diphenylphosphonyl azide, 2-ethyl-7-hydroxybenzisoxazolium salts, 2-ethyl-5-(m-sulfonyl)isoxazolium hydroxide inner salts, (chloromethylene)dimethyl ammonium chloride and the like.

Examples of salts of compounds of the formula (III) include an alkali metal salt or an alkaline earth metal salt (for example, the sodium, potassium, calcium, etc., salts) of acids of the formula (III); organic amine salts (for example, trimethylamine, triethylamine, quinoline, collidine, etc., salts) of the acids of the formula (III); and organic sulfonic acid salts (for example, toluenesulfonic acid, naphthalenesulfonic acid, tetralinsulfonic acid, trifluoroacetic acid, hydrochloric acid, etc., salts) of the acids of the formula (III).

The derivatives of the compounds of the formula (III) can be carboxyl-protected derivatives in which the carboxyl group is protected with a conventional protecting group, and such derivatives may be in the form of the ester, amide or anhydride thereof.

Examples of these carboxyl-protected derivatives include a silyl ester, an organo-tin ester, a toluenesulfonyl ethyl ester, a p-nitrobenzyl ester, a benzyl ester, a phenacyl ester, a 2-furylmethyl ester, a diphenylmethyl ester, a substituted diphenylmethyl ester, a p-methoxybenzyl ester, a trityl ester, a benzoyloxymethyl ester, a lower alkanoyloxymethyl ester, a dimethylmethyleneamino ester, a p-nitrophenyl ester, a methylsulfonylphenyl ester, a methylthiophenyl ester, a t-butyl ester, a 4-picolyl ester, an iodoethyl ester, a trichloroethyl ester, a phthalimidomethyl ester, a 3,4-dimethoxy or 3,5-dimethylbenzyl ester, a 2-nitrobenzyl ester, a 2,2'-dinitrobenzyl ester, an acetyloxycarbonyl group, or a trichloroethyl ester thereof, and the compounds of the formula (III) in which the carboxyl group is protected with a group of the formula

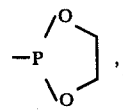

a group of the formula —N=CH—R' (in which R' is an alkyl group or an aryl group), or a group of the formula

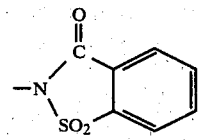

In case of the silyl ester, other substituents of the compound of the formula (III), if any, such as a hydroxy group or an amino group may be silylated.

In case of these derivatives of compounds of the formula (III), their hydrochloric acid, p-toluenesulfonic acid, naphthalene sulfonic acid or tetralin sulfonic acid salts may also be used.

The carboxyl-protecting group can be removed after the reaction under mild conditions, if necessary. For example, it can be removed by a solvolysis such as a hydrolysis and an alcoholysis, a catalytic hydrogenation, a reduction, an oxidation, a nucleophilic substitution reaction, a photochemical reaction or an enzymatic reaction.

The reaction between the acid of the formula (II) or the reactive derivative thereof and the compound of the formula (III) or the derivative thereof can generally be carried out at a temperature ranging from about −50° to about 50° C.

The starting material compounds of the formula (II) and their reactive derivatives are known compounds and can be prepared by known methods, e.g., as described in *J. Am. Chem. Soc.*, 68, 1317 (1946); *J. Chem.*

Soc., (c), 1966, 1816; *J. Chem. Soc.*, 1953, 4175; *Helvetica Chimica Acta*, 37, 134 (1954); *Chem. Pharm. Bull.*, 19 (7), 1482-6 (1971); *J. Am. Chem. Soc.*, 78, 1938 (1956); *J. Het. Chem.*, 9, 235 (1972); *Roczuiki Chemii*, 48 (2) 321-4 (1974). The starting material compounds of the formula (III) wherein T is a group represented by —CH$_2$—S—Het can be prepared in a conventional manner by reacting a compound of the formula (IV):

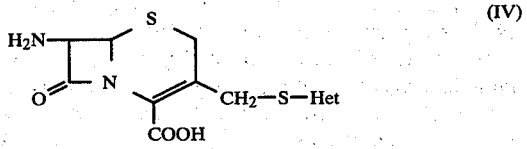

wherein Het is as defined above, with a compound of the formula (V):

wherein R is as defined above.

This process can be carried out in substantially the same manner as the process of reacting the compound of the formula (II) with the compound of the formula (III).

The compounds of the formula (III) wherein T is

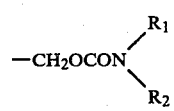

and R$_1$ and R$_2$ are as defined above can be prepared by the method as described in German Patent Publication (DT-OS) No. 2,203,653.

The compounds of the formula (III) wherein T is —CH$_2$—S—D (where D is as defined above) can be prepared by the method as described in Japanese Patent Application (OPI) Nos. 54580/76 and 88990/76.

The compounds of the formula (III) wherein T is —CH$_2$N$_3$ can be prepared by the method as described in British Pat. No. 1,297,069.

An alternative method for preparing the compounds of the formula (I) comprises reacting an acylaminocarboxylic acid of the formula (VI):

wherein A and R are as defined above, or a reactive derivative thereof, with a compound of the formula (VII):

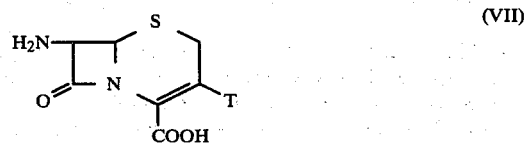

wherein T is as defined above, or a derivative thereof, to produce the compound of the formula (I).

The above reaction can be carried out under the reaction conditions set forth for the reaction between the compound of the formula (II) and the compound of the formula (III).

The compounds of the formula (VI) described above are known compounds and can be prepared by a conventional method (e.g., as described in U.S. Pat. No. 3,954,733).

The compounds of the formula (VII) as described above can be prepared by known methods as described in Japanese Patent Application (OPI) No. 58089/75, Japanese Patent Publication No. 5550/72, British Pat. No. 1,297,069 and German Patent Publication (DT-OS) No. 2,203,653.

An alternative method for preparing the compounds of the formulae (I-a) and (I-c) comprises reacting an N-acylamino-α-arylacetamidocephalosporin of the formula (VIII):

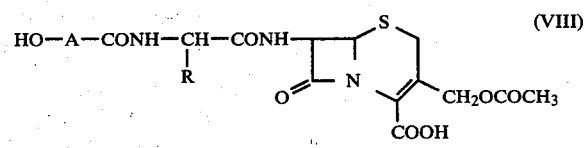

wherein A and R are as defined above, with a thiol compound of the formula (IX):

wherein U represents Het or D, each of which is as defined above, to produce a compound of the formula (I-a) or (I-c):

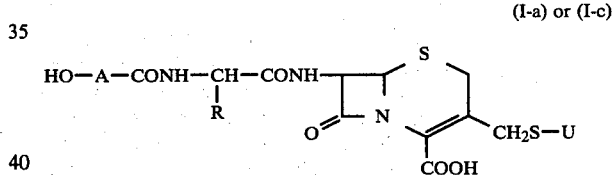

wherein A, R and U are as defined above, using a conventional procedure as described in, for example, Japanese Patent Publication Nos. 12136/71, 2340/71 and 14734/71, Japanese Patent Application (OPI) No. 68593/73, *J. Chem. Soc.*, 1965, p5015, etc.

For example, the reaction can be carried out in an inert solvent such as water. Organic solvents such as acetone, acetonitrile, methanol, ethanol, dimethylformamide and the like may be used in combination with water and a suitable buffer may also be used. When the compounds of the formula (VIII) are used in the form of the free carboxylic acid, the reaction preferably is carried out in the presence of a base such as sodium bicarbonate or triethylamine. In general, the reaction is preferably conducted at about 50° C. to about 60° C.

A still alternative method for preparing the compounds of the formulae (I-a) and (I-c) comprises reacting a compound of the formula (X):

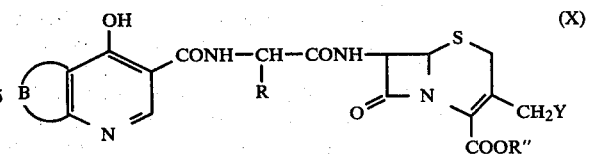

wherein B and R are as defined above; Y represents a halogen atom or an

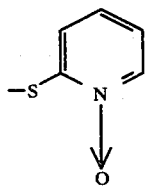

moiety; and R" represents a hydrogen atom or an ester group which is capable of being easily removed, with a heterocyclic thiol compound of the formula (IX):

HS—U   (IX)

wherein U is as defined above, as disclosed in, for example, Japanese Patent Application (OPI) No. 117487/74. That is, the reaction between the compound of the formula (X) and the heterocyclic thiol compound can be effected in a solvent such as dimethylformamide, hexamethylphosphoric triamide and the like, in the presence of a metal compound such as cupric chloride, cupric bromide, cupric fluoride, copper sulfate and the like, at a temperature of about 0° C. to about 100° C.

Another method for preparing the compound of the formula (I-d) comprises reacting an N-acylamino-α-arylacetamidocephalosporin of the formula (XI):

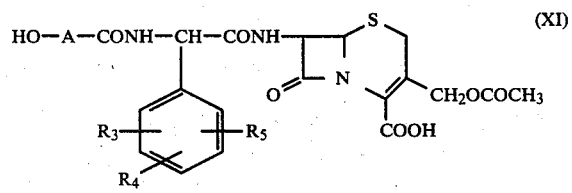

wherein A, $R_3$, $R_4$ and $R_5$ are as defined above, with sodium azide ($NaN_3$) to produce the corresponding compound of the formula (I), as described, for example, in *J. Chem. Soc.*, 1965, 5015. More specifically, the above reaction can be effected using a solvent such as water, preferably a buffer solution, or a mixture thereof with an organic solvent, e.g., as described above, at a temperature of about 50° C. to about 60° C.

Also, an alternative method for preparing the compound of the formula (I-b) comprises reacting a compound of the formula (XII):

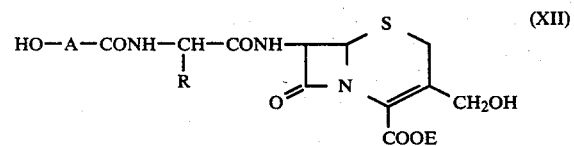

wherein A and R are as defined above, and E represents an ester residue which is capable of being easily removed, with a compound of the formula (XIII):

XCONH₂   (XIII)

wherein X represents a halogen atom, or a compound of the formula (XIV):

ZSiNCO   (XIV)

wherein Z represents a hydrogen atom or a methoxy group, to produce the corresponding compound of the formula (I), as disclosed in, for example, Dutch Patent Publication Nos. 7,216,136 and 7,216,137.

The compounds of the formula (I) of this invention are valuable as antibacterial agents, nutritional supplements in animal feeds, therapeutic agents for poultry and animals, including man, and are especially useful in the treatment of infectious diseases caused by Gram-positive bacteria such as *Staphylococcus aureus, Staphylococcus epidermidis, Staphylococcus pyogenes, Diplococcus pneumoniae, Sarcina lutea, Bacillus subtilis, Clostridium perfringens* and *Corynebacterium diphtheriae*, and Gram-negative bacteria such as *Escherichia coli, Neisseria gonouhoeae, Salmonella typhi, Klebsiella pneumoniae, Shigella dysenteriae, Shigella flexneri, Shigella sonnei, Enterobacter aerogenes, Proteus mirabilis, Proteus valgaris, Pseudomonas aeruginosa* and *Serratia marcescens*. For the treatment or prevention of such infectious diseases, the compounds of this invention, either individually or in combination with a pharmaceutically acceptable carrier or diluent, or another active ingredient(s), e.g., another chemotherapeutic agent(s), can be administered intramuscularly or intravenously to a subject.

The dosage of the compounds of the formula (I) of this invention will vary with the body weight, age and conditions of an individual subject, the kind of bacteria, and the pharmacokinetic properties of the particular compound chosen. Although the particular dosage will be determined by a physician taking these factors into consideration, the compounds of the formula (I) are, in general, most desirably administered intramuscularly or intravenously at a dosage ranging from about 2 mg/kg of body weight/day to 400 mg/kg of body weight/day, preferably from 8 mg/kg of body weight/day to 120 mg/kg of body weight/day in a single dose or in multiple doses 1 to 5 times daily.

For intramuscular or intravenous administrations the compounds of this invention may be used in the form of sterile solution or suspension containing additionally a pharmaceutically acceptable diluent or carrier such as water, saline solution, Ringer's solution, glycerin, polyethylene glycol, etc. These preparations or formulations may also contain suitable auxiliary materials, such as stabilizers, buffer substances, wetting agents, emulsifiers, local anesthetics, or salts that regulate the osmotic pressure. The compounds of the formula (I) of this invention may also be applied topically in the form of an ointment or cream to the skin or other organs as a sterilizer or disinfectant.

The present invention is further illustrated in greater detail by the following Examples and Reference Examples, but the invention is not to be construed as being limited thereto. Unless otherwise indicated, all parts, percents and ratios are by weight.

EXAMPLE 1

Preparation of
7-[D-α-(4-Hydroxy-1,5-naphthyridine-3-carboxamido)-α-p-hydroxyphenylacetamido]-3-(tetrazolo-[4,5-b]pyridazine-6-ylthiomethyl)-3-cephem-4-carboxylic Acid

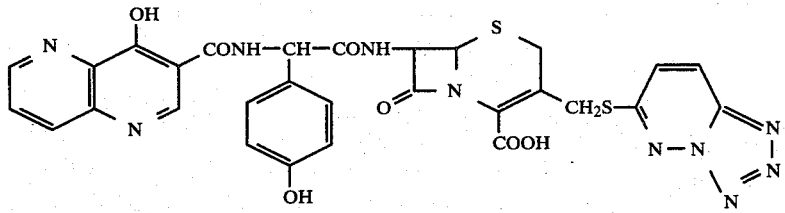

1.23 g of sodium 7-[D-α-(4-hydroxy-1,5-naphthyridine-3-carboxamido)-α-p-hydroxyphenylacetamido]-3-acetoxymethyl-3-cephem-4-carboxylate, 0.20 g of sodium bicarbonate and 20 ml of a phosphate buffer (pH 6.4) were heated at a temperature of 60° C., and a solution of 0.416 g of 6-mercaptotetrazolo[4,5-b]pyridazine in 10 ml of acetone was added dropwise thereto. After completion of the dropwise addition, the resulting mixture was allowed to react for 12 hours and 20 minutes at the same temperature. The thus obtained homogeneous reaction solution was then ice cooled whereby crystals precipitated. The crystals thus precipitated were filtered, washed with 95% ethanol and dried over phosphorus pentoxide under reduced pressure to obtain 0.38 g of the titled compound as the sodium salt.

Melting Point: 267°–274° C. (decomposition).
IR Absorption: $\nu_{Nujol}cm^{-1}$ 1770, 1650, 1610.

EXAMPLE 2

Preparation of
7-[D-α-(4-Hydroxy-1,5-naphthyridine-3-carboxamido)-α-p-hydroxyphenylacetamido]-3-(pyrido[2,1-c]-s-triazol-3-ylthiomethyl)-3-cephem-4-carboxylic Acid

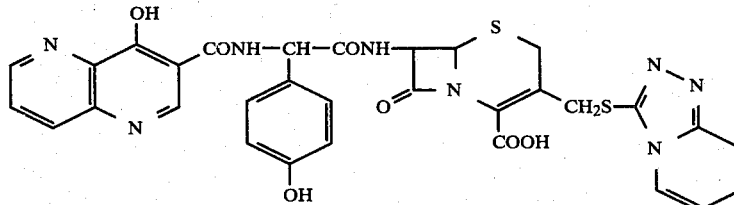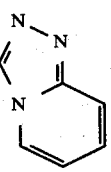

1.23 g of sodium 7-[D-α-(4-hydroxy-1,5-naphthyridine-3-carboxamido)-α-p-hydroxyphenylacetamido]-3-acetoxymethyl-3-cephem-4-carboxylate, 0.45 g of sodium bicarbonate, 20 ml of a phosphate buffer (pH 6.4), 0.906 g of 3-mercaptopyrido[2,1-c]-s-triazole and 20 ml of acetone were charged into a reactor, and the resulting mixture was allowed to react for 23 hours at a temperature of 60° C. with stirring. The reaction solution was then cooled and adjusted to a pH of 3.2 to 3.6 with 6 N hydrochloric acid. After stirring the mixture under ice cooling, the precipitated crystals were filtered, washed with water and dried over phosphorus pentoxide under reduced pressure to obtain 0.88 g of the titled compound.

Melting Point: 221°–224° C. (decomposition).
IR Absorption: $\nu_{Nujol}cm^{-1}$ 1760, 1655, 1610.

EXAMPLE 3

Preparation of
7-[D-α-(4Hydroxypyridine-3-carboxamido)-α-p-hydroxyphenylacetamido]-3-(tetrazolo[4,5-b]pyridazine-6-ylthiomethyl)-3-cephem-4-carboxylic Acid

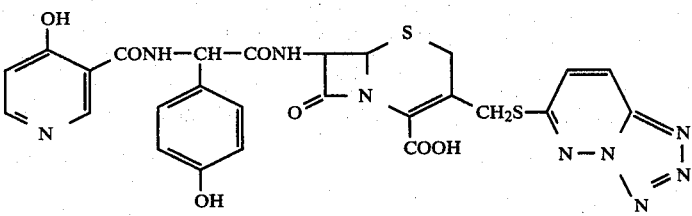

To a solution of 9 ml of dimethyl sulfoxide, 0.606 g of triethylamine and 0.472 g of 4-hydroxypyridine-3-carboxylic acid N-hydroxysuccinimide ester was added 1.25 g of the trifluoroacetic acid salt of 7-(D-α-amino-α-p-hydroxyphenylacetamido)-3-(tetrazolo[4,5-b]pyridazine-6-ylthiomethyl)-3-cephem-4-carboxylic acid, and the mixture was allowed to react for 12 minutes at room temperature (about 20°–30° C.). The reaction solution was then added dropwise to 200 ml of acetone, and 100 ml of diethyl ether was further added thereto whereby the crystals thus precipitated where filtered to obtain 0.99 g (yield: 70.2%) of the titled compound as the triethylamine salt.

The resulting triethylamine salt was dissolved in 10 ml of water and then the solution was adjusted to a pH of 3 with 2 N hydrochloric acid with stirring under ice cooling. To the thus-obtained gel-like crystals were further added 15 ml of water and 6 ml of methanol to thereby effect acid crystal formation. The precipitated crystals were filtered, washed with methanol and dried over phosphorus pentoxide under reduced pressure to obtain 0.84 g of the titled compound.

The resulting compound was dissolved in 8 ml of dimethyl sulfoxide, and 0.26 g of sodium 2-ethylhexanoate was added thereto followed by stirring the mixture for 20 minutes at room temperature. The reaction solution was then added dropwise to 200 ml of acetone. The precipitated crystals were filtered, washed successively with acetone and diethyl ether and dried over phosphorus pentoxide under reduced pressure to obtain 0.85 g of the titled compound as the sodium salt.

Melting Point: 253°–257° C. (decomposition).

IR Absorption: $\nu_{Nujol}{}^{cm^{-1}}$ 1760, 1660, 1630, 1610.

EXAMPLE 4

Preparation of 7-[D-α-(4-Hydroxypyridine-3-carboxamido)-α-p-hydroxyphenylacetamido]-3-carbamoyloxymethyl-3-cephem-4-carboxylic Acid

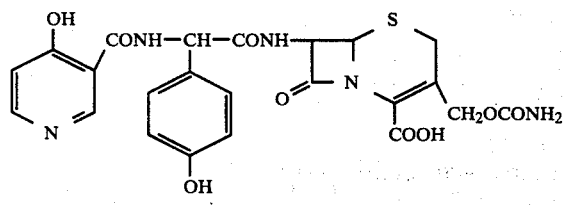

4.22 g of 7-(D-α-amino-α-p-hydroxyphenylacetamido)-3-(carbamoyloxymethyl)-3-cephem-4-carboxylic acid, 2.02 g of triethylamine and 30 ml of dimethyl sulfoxide were stirred at room temperature, and 2.36 g of 4-hydroxypyridine-3-carboxylic acid N-hydroxysuccinimide ester was then added thereto whereby the mixture was allowed to react for 20 minutes at the same temperature with stirring. Thereafter, 1.66 g of sodium 2-ethylhexanoate was added to the resulting reaction mixture, and 10 minutes later the reaction solution was added dropwise to 500 ml of acetone. The precipitated titled compound as the sodium salt was filtered and dried over phosphorus pentoxide under reduced pressure to obtain 3.82 g of the dried product.

EXAMPLES 5 TO 12

The following compounds were synthesized in the same manner as described in Example 4.

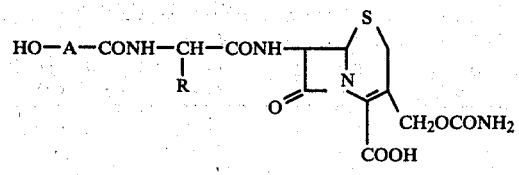

| Example No. | HO—A— | —R |
|---|---|---|
| 5 | 4-hydroxypyridin-3-yl | 3-aminophenyl |
| 6 | 4-hydroxypyridin-3-yl | phenyl |
| 7 | 4-hydroxy-1,5-naphthyridin-3-yl (or similar) | 4-hydroxyphenyl |
| 8 | 4-hydroxy pyridopyridinyl | phenyl |
| 9 | 4-hydroxy pyridopyridinyl | 3-aminophenyl |
| 10 | 2-methylthio-pyrimidopyridin-hydroxyl | 4-hydroxyphenyl |
| 11 | 4-hydroxy pyrimidopyridinyl | 4-hydroxyphenyl |
| 12 | 4-hydroxy pyridopyridinyl | 3-chloro-4-hydroxyphenyl |

The results of the antimicrobial activities of these compounds in in vitro testing in accordance with the recognized method are set forth in the Table below.

TABLE

| Example No. | Minimum Inhibitory Concentration (μg/ml) | | | | | |
|---|---|---|---|---|---|---|
| | Staphylococcus aureus 209P | Staphylococcus aureus FS 289 | Escherichia coli NIHJ | Klebsiella pneumoniae 602 | Proteus vulgaris HX-19 | Pseudomonas aeruginosa 104 |
| 4 | 0.39 | 3.13 | 12.5 | 12.5 | 0.2 | 6.25 |
| 5 | 0.39 | 3.13 | 6.25 | 12.5 | 0.2 | 6.25 |
| 6 | 0.39 | 3.13 | 12.5 | 12.5 | 0.2 | 12.5 |
| 7 | 0.78 | 6.25 | 3.13 | 1.56 | 0.78 | 6.25 |
| 8 | 0.78 | 6.25 | 3.13 | 1.56 | 0.78 | 6.25 |
| 9 | 0.78 | 3.13 | 1.56 | 1.56 | 0.78 | 6.25 |
| 10 | 0.78 | 3.13 | 6.25 | 6.25 | 1.56 | 6.25 |
| 11 | 1.56 | 6.25 | 6.25 | 6.25 | 1.56 | 12.5 |
| 12 | 1.56 | 6.25 | 3.13 | 1.56 | 0.78 | 6.25 |

EXAMPLE 13

Preparation of 7-[D-α-(4-Hydroxy-1,5-naphthyridine-3-carboxamido)-α-p-hydroxyphenylacetamido]-3-(5-carboxymethyl-1,3,4-thiadiazol-2-ylthiomethyl)-3-cephem-4-carboxylic Acid

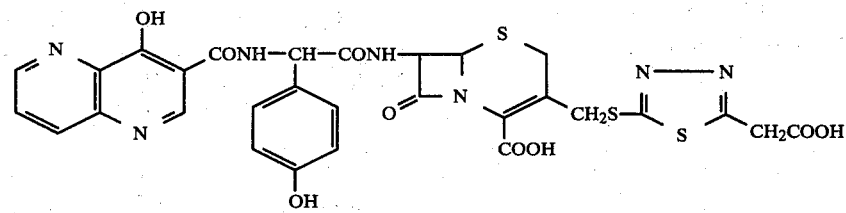

1.23 g of sodium 7-[D-α-(4-hydroxy-1,5-naphthyridine-3-carboxamido)-α-p-hydroxyphenylacetamido]-3-acetoxymethyl-3-cephem-4-carboxylate, 0.20 g of sodium bicarbonate and 20 ml of a phosphate buffer (pH 6.4) were heated at a temperature of 60° C., and a solution of 0.48 g of (5-mercapto-1,3,4-thiadiazol-2-yl)acetic acid in 10 ml of acetone was added dropwise thereto. The resulting mixture was then allowed to react for 15 hours at the same temperature. The reaction solution was cooled and acidified with 6 N hydrochloric acid. The formed precipitate was filtered and washed with water to obtain the titled compound. The resulting product was converted into the sodium salt using sodium 2-ethylhexanoate in a usual manner.

IR Absorption: $v_{Nujol}^{cm^{-1}}$ 1770, 1650, 1610.

The antimicrobial activities of this compound were as follows.

| | |
|---|---|
| Staphylococcus aureus 209 P | 0.78 μg/ml |
| Escherichia coli NIHJ | 1.56 μg/ml |
| Klebsiella pneumoniae 602 | 1.56 μg/ml |
| Pseudomonas aeruginosa 104 | 3.13 μg/ml |

EXAMPLE 14

Preparation of 7-[D-α-(4-Hydroxy-1,5-naphthyridine-3-carboxamido)-α-p-hydroxyphenylacetamido]-3-(1-carboxymethyl-1,2,3,4-tetrazol-5-ylthiomethyl)-3-cephem-4-carboxylic Acid

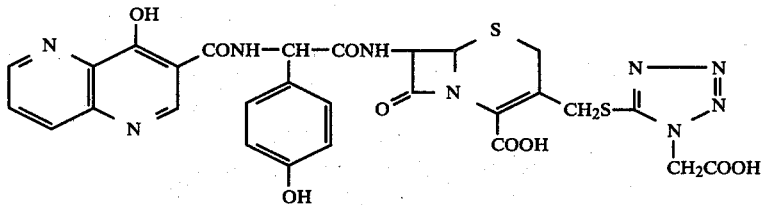

The titled compound as the sodium salt was prepared in the same manner as described in Example 13 but using 5-mercapto-1H-tetrazol-1-acetic acid in place of (5-mercapto-1,3,4-thiadiazol-2-yl)acetic acid.

IR Absorption: $v_{Nujol}^{cm^{-1}}$ 1765, 1655, 1610.

The antimicrobial activities of this compound were as follows.

| | |
|---|---|
| Staphylococcus aureus 209 P | 0.78 μg/ml |
| Escherichia coli NIHJ | 1.56 μg/ml |
| Klebsiella pneumoniae 602 | 1.56 μg/ml |
| Pseudomonas aeruginosa 104 | 3.13 μg/ml |

EXAMPLE 15

Preparation of
7-[D-α-(4-Hydroxy-1,5-naphthyridine-3-carboxamido)-α-p-hydroxyphenylacetamido]-3-azidomethyl-3-cephem-4-carboxylic Acid

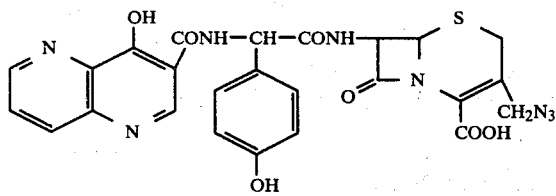

A solution of 2.0 g of the sodium salt of 7-[D-α-(4-hydroxy-1,5-naphthyridine-3-carboxamido)-α-p-hydroxyphenylacetamido]-3-acetoxymethyl-3-cephem-4-carboxylic acid, 0.328 g of sodium bicarbonate, 0.635 g of sodium azide and 40 ml of a phosphate buffer (pH 6.4) was allowed to react for 18 hours at a temperature of 55° C. with stirring. The insoluble matter was filtered out with heating, and the filtrate was then allowed to stand at room temperature whereby the turbidity formed was filtered out. The resulting reaction solution was then adjusted to a pH of 2 with 6 N hydrochloric acid, and the precipitated crystals were filtered and dried over phosphorus pentoxide under reduced pressure to obtain 0.80 g of the titled compound.

This compound was dissolved in 5 ml of dimethyl sulfoxide, and the resulting mixture was reprecipitated with 30 ml of methanol to obtain 0.55 g of the purified product.

The resulting product was further dissolved in 3 ml of dimethyl sulfoxide, and 0.168 g of sodium 2-ethylhexanoate was added thereto. After stirring the mixture for 10 minutes, 30 ml of acetone was further added dropwise thereto. The precipitated sodium salt was filtered, washed with acetone and dried over phosphorus pentoxide under reduced pressure to obtain 0.50 g of the titled compound as the sodium salt.

Melting Point: 283°–290° C. (decomposition).
IR Absorption: $\nu_{Nujol}\,cm^{-1}$ 2100, 1765, 1650, 1610.

EXAMPLE 16

Preparation of
7-[D-α-(4-Hydroxy-1,5-naphthyridine-3-carboxamido)-α-p-hydroxyphenylacetamido]-3-azidomethyl-3-cephem-4-carboxylic Acid To a suspension of 1.43 g of 4-hydroxy-1,5-naphthyridine-3-carboxylic acid N-hydroxysuccinimide ester, 1.01 g of triethylamine and 30 ml of dimethyl sulfoxide was added 2.11 g of 7-(D-α-amino-p-hydroxyphenylacetamido)-3-aminocarbonyloxymethyl-3-cephem-4-carboxylic acid, and the mixture was allowed to react for 40 minutes at room temperature with stirring. A slight amount of insoluble materials was then filtered out, and the filtrate was added dropwise to 600 ml of acetone. The precipitated crystals were filtered and dried over phosphorus pentoxide under reduced pressure to obtain 2.7 g of the titled compound as the triethylamine salt. The sodium salt of the titled compound was prepared using sodium 2-ethylhexanoate in the same manner as described in Example 15.

The resulting product was the same as that obtained in Example 15 and showed the same IR absorption, NMR spectrum and Rf value (thin layer chromatography using a silica gel plate).

EXAMPLE 17

Preparation of
7-[D-α-(4-Hydroxy-1,5-naphthyridine-3-carboxamido)-α-p-hydroxyphenylacetamido]-3-aminocarbonyloxymethyl-3-cephem-4-carboxylic Acid 1.70 g of D-α-(4-hydroxy-1,5-naphthyridine-3-carboxamido)-α-p-hydroxyphenyl-acetic acid, which can be synthesized by the synthesis method as disclosed in U.S. Pat. No. 3,954,733, was dissolved in 60 ml of dimethyl sulfoxide, and 0.89 g of N,N'-carbonyldiimidazole was added to the resulting mixture at room temperature with stirring. 30 minutes later a solution of 1.36 g of 7-amino-3-aminocarbonyloxymethyl-3-cephem-4-carboxylic acid, 0.76 g of triethylamine and 30 ml of dimethyl sulfoxide was added thereto followed by allowing the mixture to react for 6 hours with stirring. The reaction solution was then added to 1.5 l of acetone, and the precipitate formed was filtered. The filtered product was dissolved in 50 ml of water and the solution adjusted to a pH of 2 with 3 N hydrochloric acid under ice cooling. The thus formed precipitate was filtered, washed with water and dried over phosphorus pentoxide under reduced pressure to obtain 1.8 g of the titled compound. The sodium salt of this product which was obtained using sodium 2-ethylhexanoate was confirmed to contain the compound obtained in Example 7.

The following compounds can be also obtained in accordance with the present invention utilizing methods as described above.

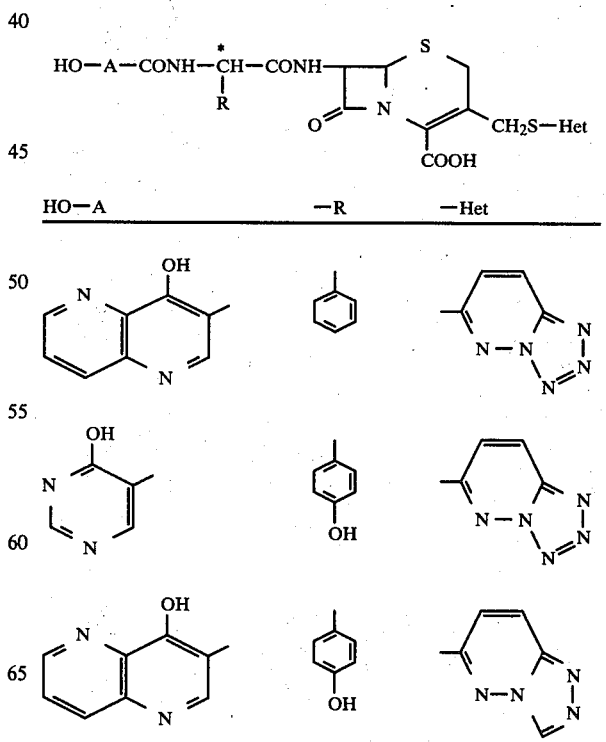

Compounds of the Formula (I-a)

-continued
Compounds of the Formula (I-a)
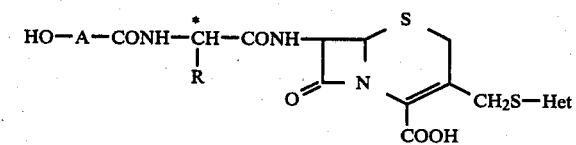
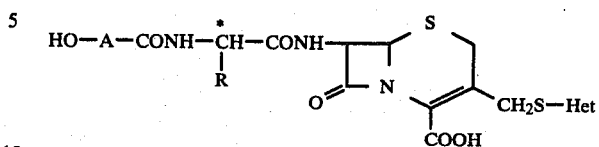
| HO—A | —R | —Het |
|---|---|---|
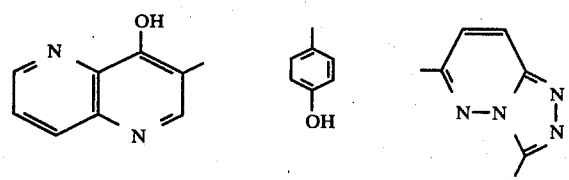
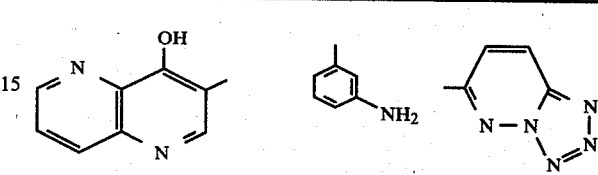
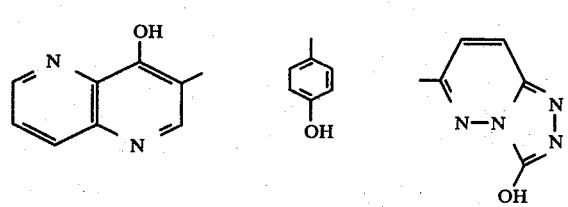
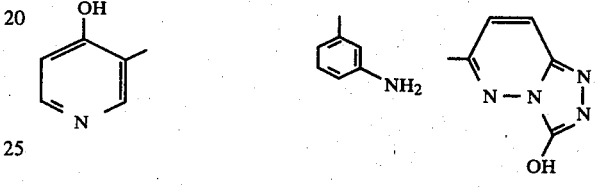
*R configuration = D-diastereomer
Compounds of the Formula (I-b)
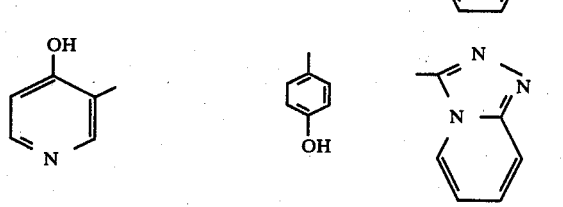
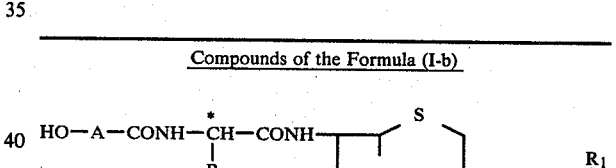
| HO—A— | —R | —N(R_1)(R_2) |
|---|---|---|
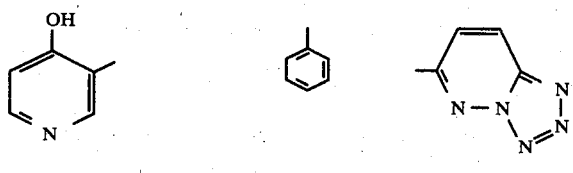
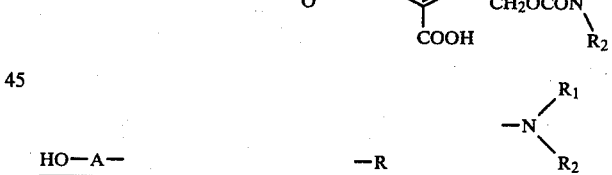
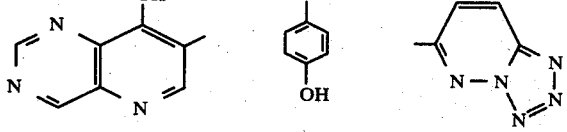
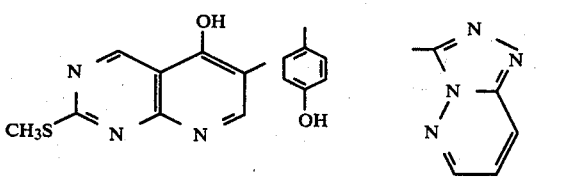
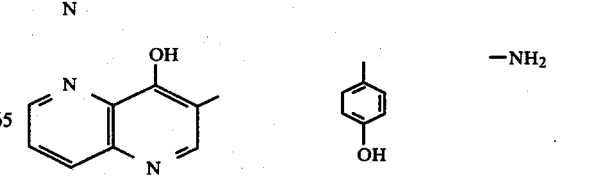

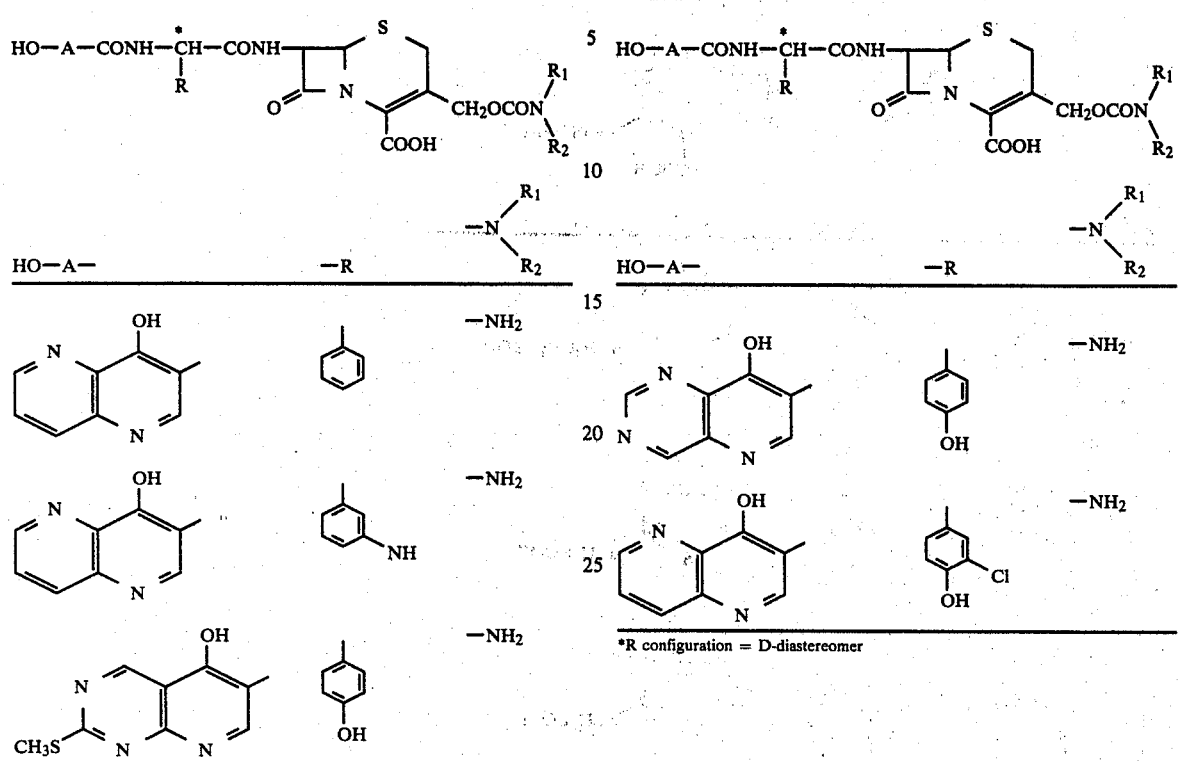
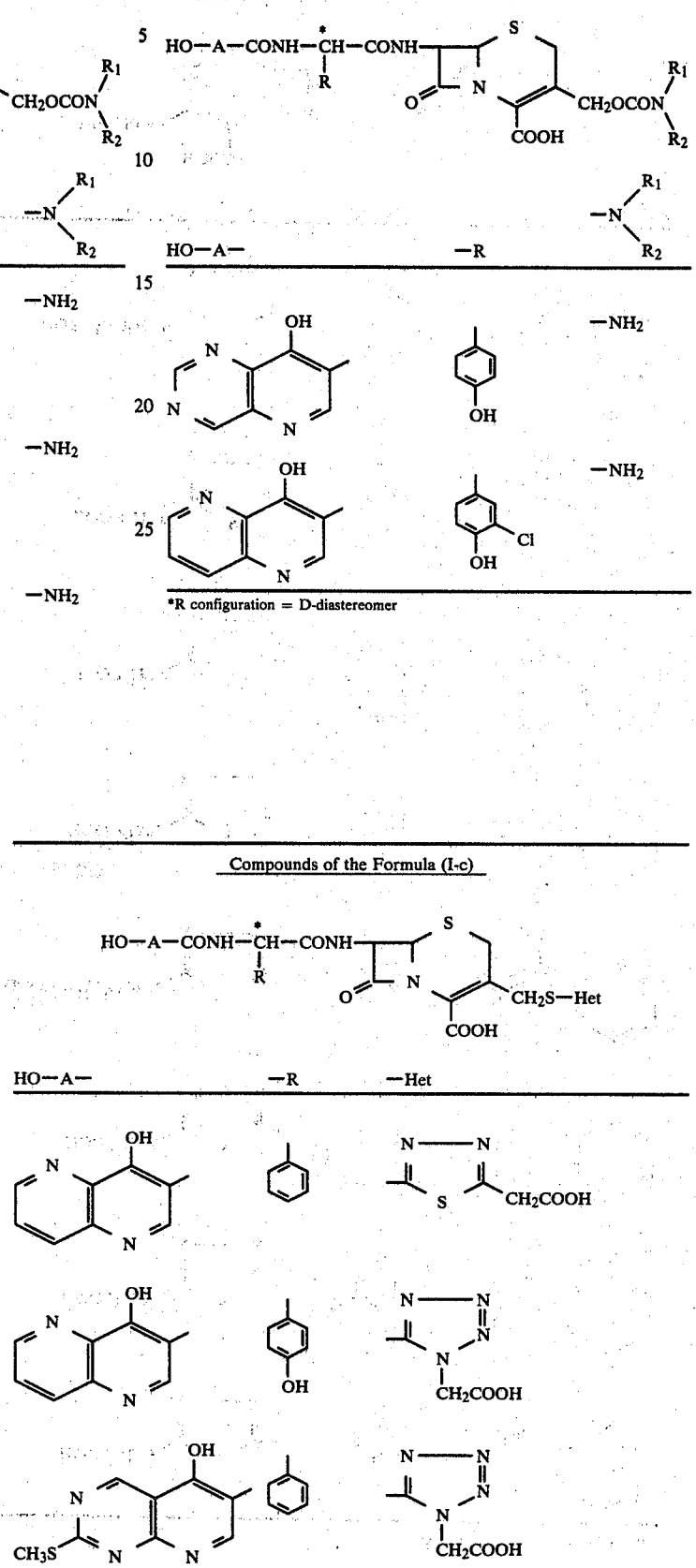

-continued
Compounds of the Formula (I-c)
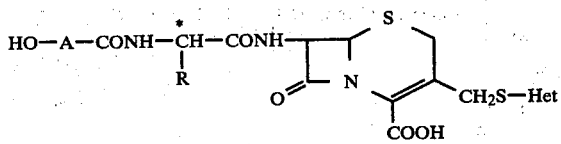
| HO—A— | —R | —Het |
|---|---|---|
| 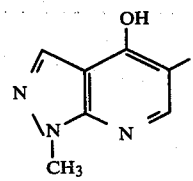 |  | 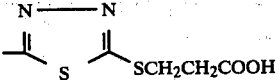 |
| 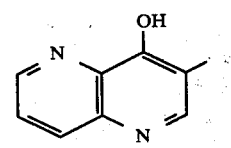 | 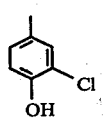 | 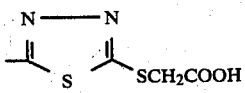 |
| 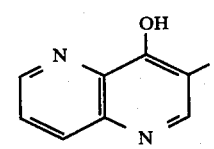 | 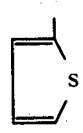 | 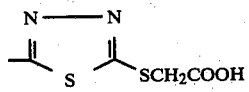 |
| 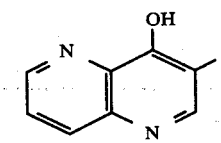 | 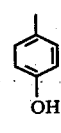 | 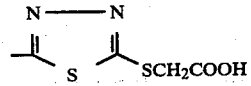 |
| 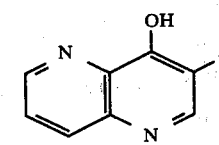 | 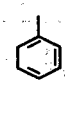 | 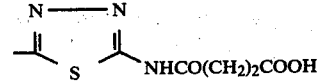 |
| 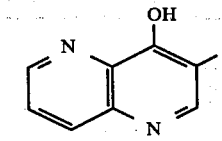 | 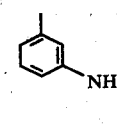 | 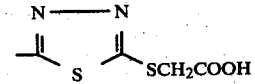 |
| 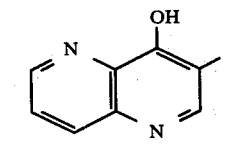 | 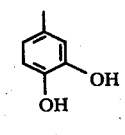 | 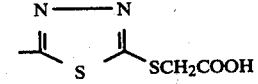 |
| 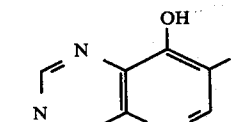 | 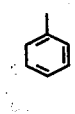 | 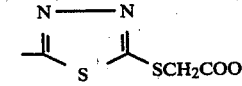 |
*R configuration = D-diastereomer

| Compounds of the Formula (I-d) | | |
|---|---|---|
| 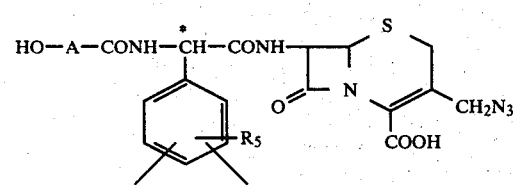 | | |
| HO—A | R3 R4 R5 | |
| 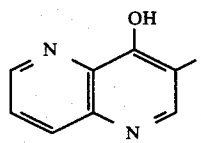 | 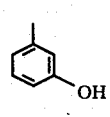 | |
| 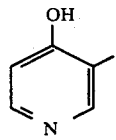 | 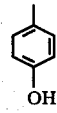 | |
| 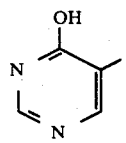 | 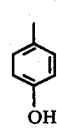 | |
| 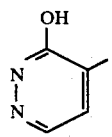 | 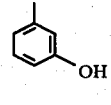 | |
| 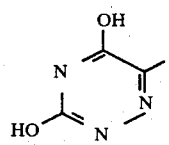 | 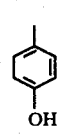 | |
| 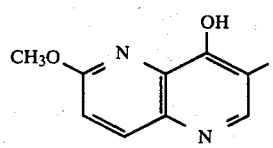 | 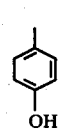 | |
| 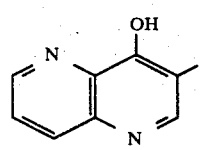 | 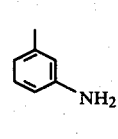 | |
| 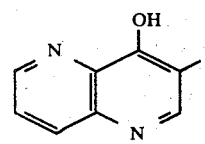 | 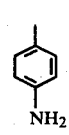 | |

-continued

| Compounds of the Formula (I-d) | |
|---|---|
| 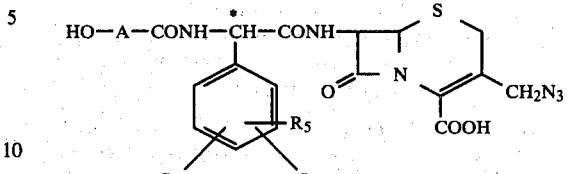 | |
| HO—A | R3 R4 R5 |
| 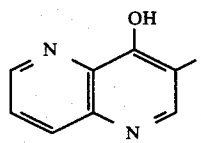 | 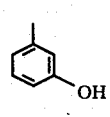 |
|  | 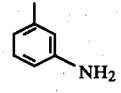 |
| 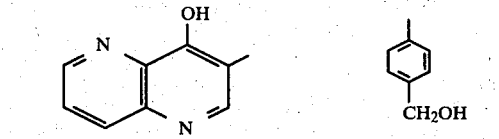 | 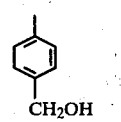 |
|  | 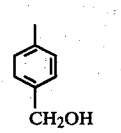 |
| 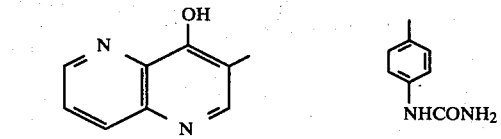 | 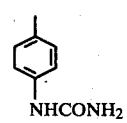 |

*configuration = D-diastereomer

The following Reference Examples are given to illustrate the preparation of the starting materials used to prepare compounds of the present invention and the others are prepared in the same manner.

REFERENCE EXAMPLE 1

Preparation of 7-[D-α-(4-Hydroxy-1,5-naphthyridine-3-carboxamido)-α-p-hydroxyphenylacetamido[-3-acetoxymethyl-3-cephem-4-carboxylic Acid 0.965 g of the trifluoroacetic acid salt of 7-(D-α-amino-α-p-hydroxyphenylacetamido)-3-acetoxymethyl-3-cephem-4-carboxylic acid was dissolved in 8 ml of dimethyl sulfoxide, and 0.545 g of triethylamine was added thereto. Subsequently, 0.516 g of 4-hydroxy-1,5-naphthyridine-3-carboxylic acid N-hydroxysuccinimide ester was added thereto followed by stirring the mixture for 1 hour and 15 minutes at room temperature. 0.598 g of sodium 2-ethylhexanoate was then added to the resulting solution, and the mixture was stirred for 10 minutes followed by filtering out the insoluble material. 100 ml of acetone was added to the filtrate, and the precipitated crystals were then filtered and dried over phosphorus pentoxide under reduced pressure to obtain 0.93 g of the titled compound as the sodium salt having a melting point (decomposition) of 261° to 265° C.

REFERENCE EXAMPLE 2

Preparation of 7-[D-α-(4-Hydroxypyridine-3-carboxamido)-α-p-hydroxyphenylacetamido]-3-acetoxymethyl-3-cephem-4-carboxylic Acid To a solution of 6 ml of dimethyl sulfoxide, 0.566 g of triethylamine and 0.441 g of 4-hydroxypyridine-3-carboxylic acid N-hydroxysuccinimide ester was added 1 g of the trifluoroacetic acid salt of 7-(D-α-amino-α-p-hydroxyphenylacetamido)-3-acetoxymethyl-3-cephem-4-carboxylic acid, and the mixture was allowed to react for 14 minutes at room temperature with stirring. The reaction solution was then added dropwise to 250 ml of acetone, and 100 ml of diethyl ether was further added thereto. The precipitated crystals were filtered and dried over phosphorus pentoxide under reduced pressure to obtain 0.99 g (yield 82.5%) of the titled compound as the triethylamine salt having a melting point of 135° C. for shrinking and 142° to 147° C. for decomposition.

This triethylamine salt was added to a solution of 0.31 g of sodium 2-ethylhexanoate in 8 ml of dimethyl sulfoxide, and the mixture was stirred for 10 minutes at room temperature. Thereafter, the resulting mixture was added to 180 ml of acetone and 50 ml of diethyl ether. The precipitated crystals were filtered and dried over phosphorus pentoxide under reduced pressure to obtain the titled compound as the sodium salt having a melting point (decomposition) of 150° to 165° C.

REFERENCE EXAMPLE 3

Preparation of 7-Amino-3-(tetrazolo[4,5-b]pyridazine-6-ylthiomethyl)-3-cephem-4-carboxylic Acid

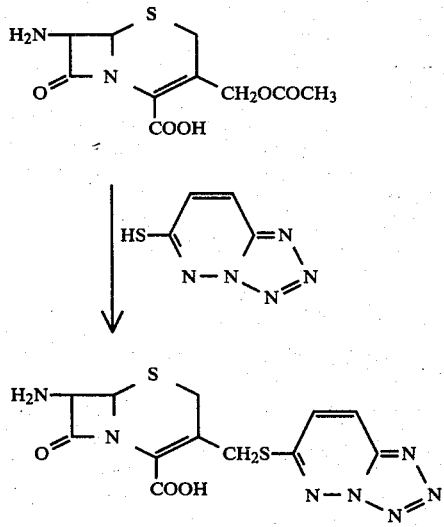

2.72 g of 7-aminocephalosporanic acid was suspended in 16 ml of water and 8 ml of acetone, and a suspension of 2.1 g of sodium bicarbonate in 16 ml of water was dropwise added thereto over a period of 7 minutes time. The inside temperature of a reactor was then increased to 50° C., and a suspension of 2.3 g of 6-mercaptotetrazolo[4,5-b]pyridazine in 35 ml of acetone was added dropwise thereto over a period of time of 10 minutes. The resulting mixture was refluxed for 6 hours at a stable inside temperature of reactor of 61° C. followed by allowing the refluxed mixture to stand. The pH of the solution was 8 and thereafter, the mixture was adjusted to a pH of 3.6 with 6 N hydrochloric acid under ice cooling, in which the pH was measured by means of a pH meter and then stirred for 1 hour. The precipitated crystals were filtered and dried over phosphorus pentoxide under reduced pressure to obtain 2.39 g of the titled compound having a melting point (decomposition) of 202° to 205° C.

REFERENCE EXAMPLE 4

Preparation of 7-Amino-3-(s-triazolo[4,5-b]pyridazine-6-ylthiomethyl)-3-cephem-4-carboxylic Acid

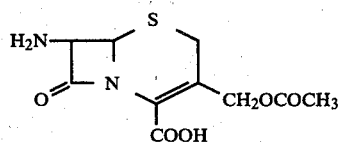

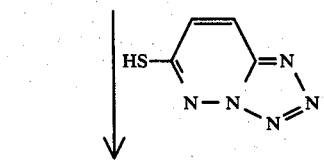

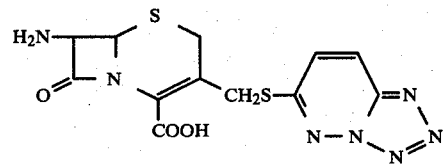

2.72 g (0.01 mol) of 7-aminocephalosporanic acid was suspended in 20 ml of water and 10 ml of acetone, and a suspension of 1.89 g of sodium bicarbonate in 10 ml of water was added dropwise thereto over a period of time of 10 minutes. The inside temperature of the reactor was then increased to 50° C., and a suspension of 1.9 g (0.0125 mol) of 2,3-triazolo-7,0-pyridazine-6-thiol in 20 ml of acetone was added dropwise thereto over a period of time of 8 minutes. The resulting mixture was refluxed for 4 hours at a stable inside temperature of the reactor of 63° C. followed by ice cooling. After the inside temperature of the reactor reached 3° to 4° C., the mixture was adjusted to a pH of 5 with 6 N hydrochloric acid under ice cooling and then stirred for 10 minutes to adjust the mixture to a pH of 3.6. One hour after the stirring, the precipitated crystals were filtered, washed with 10 ml of water and two times with 10 ml of acetone and dried over phosphorus pentoxide under reduced pressure to obtain 2.58 g (yield 72.5%) of the titled compound having a melting point (decomposition) of 187° C.

Purification

A suspension of 1 g of the thus obtained crude product in 10 ml of water was stirred under ice cooling, and 9 ml of 12 N hydrochloric acid was added dropwise thereto incrementally over a period of time of 10 minutes. Twenty minutes after the stirring, the insoluble material was filtered out, and the mother liquor was adjusted to a pH of 3.6 with 7 ml of 30% sodium hydroxide and 3 ml of 10% sodium hydroxide. Thereafter, the resulting mixture was stirred for 1 hour, and the precipitated crystals were filtered and dried over phosphorus pentoxide under reduced pressure to obtain 0.84 g (yield: 84%) of the titled compound having a melting point (decomposition) of 194° C.

The same procedure as described above was followed using 10.74 g (0.0395 mol) of 7-aminocephalosporanic acid, 134 ml of water, 7.5 g of sodium bicarbonate and 7.5 g of 2,3-triazolo-7,0-pyridazine-6-thiol to obtain 10.53 g (yield: 75%) of the titled compound as crude crystals. This compound was found to have a melting point (decomposition) of 189° to 192° C.

Subsequently, the same purification procedure described above was followed using 10 g of the thus obtained crude product to obtain 8.2 g (yield: 82%) of the purified titled compound having a melting point (decomposition) of 194° C.

REFERENCE EXAMPLE 5

Preparation of
7-Amino-3-(pyrido[2,1-c]-s-triazol-3-ylthiomethyl)-3-cephem-4-carboxylic Acid

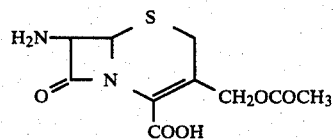

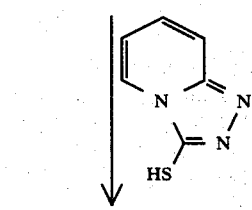

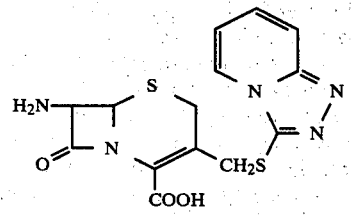

2.72 g (0.01 mol) of 7-aminocephalosporanic acid was suspended in 18 ml of water, and a suspension of 2.1 g (0.025 mol) of sodium bicarbonate in 20 ml of water was added dropwise thereto over a period of time of 10 minutes. The inside temperature of the reactor was then increased to 50° C., and a suspension of 1.81 g (0.0125 mol) of 3-mercaptopyrido[2,1-c]-s-triazole in 35 ml of acetone was added dropwise thereto over a period of time of 10 minutes. The resulting mixture was refluxed for 4 hours at a stable inside temperature of the reactor of 63° C. followed by ice cooling the mixture. After the inside temperature of the reactor reached 4° C., the mixture was adjusted to a pH of 3.6 with 6 N hydrochloric acid. One hour after the stirring, the precipitated crystals were filtered and dried over phosphorus pentoxide under reduced pressure to obtain 2.31 g (yield: 61%) of the tilted compound having a melting point (decomposition) of 173° to 175° C.

REFERENCE EXAMPLE 6

Preparation of
7-(D-α-amino-α-p-hydroxyphenylacetamido)-3-(tetrazolo[4,5-b]pyridazine-6-ylthiomethyl)-3-cephem-4-carboxylic Acid

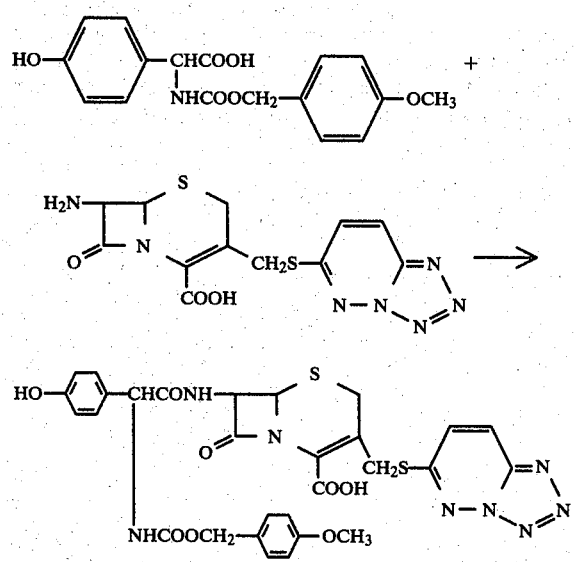

3.31 g (0.01 mol) of D(—)-N-p-methoxybenzyloxycarbonylamino-p-hydroxyphenylglycine was suspended in 25 ml of dry acetonitrile, and 1.01 g of N-methylmorpholine was added thereto. The resulting mixture was then cooled to —9° C. (inside temperature), and a solution of 1.36 g of chloroisobutyl carbonate in 2 to 3 ml of acetonitrile was added dropwise thereto. The resulting mixture was stirred for 1.5 hours at a temperauture of —5° to —9° C. Separately, 4.01 g (0.011 mol) of 7-amino-3-(tetrazolo-[4,5-b]pyridazine-6-ylthiomethyl)-3-cephem-4-carboxylic acid was suspended in 20 ml of dry acetonitrile, and 6.4 ml of N,O-bis(trimethylsilyl) acetamide was added thereto followed by stirring the mixture for 20 minutes at room temperature to obtain a disilyl compound containing solution. This disilyl compound containing solution was added at once to the above-described mixed anhydride solution, and the mixture was allowed to react for 5 hours at a temperature of —10° to —2° C. After the mixture was further stirred for an additional 20 minutes at a temperature of 0° to 8° C., 20 ml of methanol was added thereto. Thus, the insoluble material was filtered out and the filtrate was then concentrated and dried to obtain an oil. To this oil were added 1.68 g of sodium bicarbonate and 20 ml of water, and 20 ml of methanol and 40 to 50 ml of ethyl acetate were further added thereto to prepare a homogeneous solution. The resulting solution was then concentrated under reduced pressure whereby the methanol was mainly discharged, and the solution then separated into two liquid phases. The resulting aqueous phase was washed twice with 50 ml of ethyl acetate, and 50 ml of fresh ethyl acetate was then added thereover. The resulting solution was adjusted to a pH of 2 to 1 with 6 N hydrochloric acid with stirring under ice cooling. Thus, gummy materials were observed mixed therewith. The aqueous solution was extracted twice with ethyl acetate, and the resulting ethyl acetate layer was washed with a saturated sodium chloride aqueous solution and dried over magnesium sulfate to obtain 2.55 g of caramel-like crystals. Since these crystals contained a slight amount of D-N-p-methoxybenzyloxycarbonylamino-p-hydroxyphenylglycine, they were purified with ethyl acetate and diethyl ether to obtain 1.38 g of the desired compound. Further, when the gummy materials were mixed with normal butanol, crystallization took place. The resulting compound was confirmed to be 2.0 g of the fairly pure desired compound. This, with the 1.38 g obtained as described above, resulted in 3.98 g of the desired compound being obtained in a yield of 58.7%.

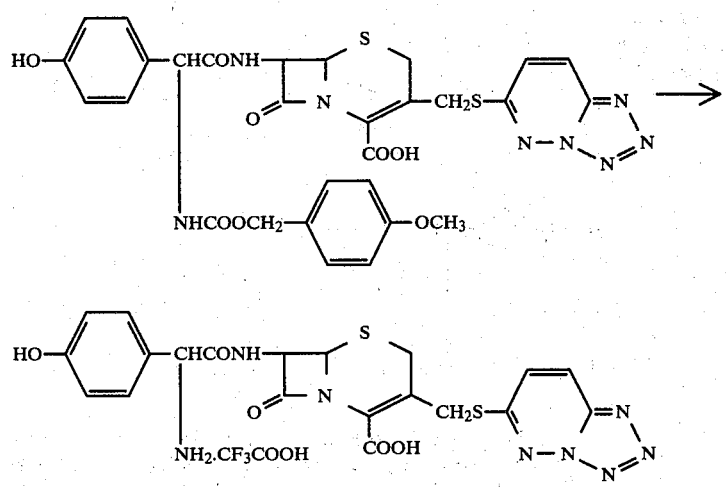

To an ice cooled solution of 16 ml of trifluoroacetic acid and 4 ml of anisole was added 2.4 g of the above-described compound, and the mixture was stirred for 35 minutes at room temperature. Thereafter, the resulting solution was added dropwise to 350 ml of diethyl ether. The precipitate formed was filtered, washed with diethyl ether and dried over phosphorus pentoxide under reduced pressure to obtain 1.94 g of the titled compound in a yield of 87.5%.

While the invention has been described in detail and with reference to specific embodiments thereof, it will be apparent to one skilled in the art that various changes and modifications can be made therein without departing from the spirit and scope thereof.

What is claimed is:

1. A compound of the formula (I-b):

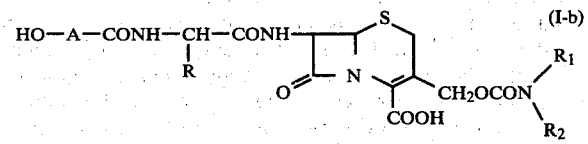

wherein A is a divalent heteroaromatic ring selected from the group consisting of a naphthyridine ring, a pyridopyrimidine ring and a pyridine ring, each of which can be unsubstituted or substituted with a $(C_1-C_4)$alkyl group or a $(C_1-C_4)$alkylthio group; R is a phenyl group which can be unsubstituted or substituted with one or two substituents selected from the group consisting of a hydroxy group, an amino group and a chlorine atom; $R_1$ and $R_2$, which can be the same or different, each is a hydrogen atom or a $(C_1-C_4)$alkyl group.

2. A compound of the formula (I-b):

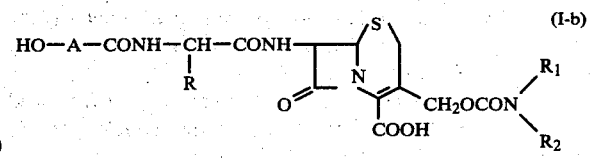

wherein A is a divalent heteroaromatic ring selected from the group consisting of a naphthyridine ring, a pyridopyrimidine ring and a pyridine ring, each of which can be unsubstituted or substituted with a $(C_1-C_4)$alkylthio group; R is a phenyl group which can be unsubstituted or substituted with one or two substituents selected from the group consisting of a hydroxy group, an amino group and a chlorine atom; and $R_1$ and $R_2$ each is a hydrogen atom.

3. 7-[D-α-(4-Hydroxypyridine-3-carboxamido)-α-(p-hydroxyphenyl)acetamido]-3-carbamoyloxymethyl-3-cephem-4-carboxylic acid and the non-toxic, pharmaceutically acceptable salts thereof, of claim 1.

4. 7-[D-α(4-Hydroxypyridine-3-carboxamido)-α-(m-aminophenyl)acetamido]-3-carbamoyloxymethyl-3-cephem-4-carboxylic acid and the non-toxic, pharmaceutically acceptable salts thereof, of claim 1.

5. 7-[D-α-(4-Hydroxypyridine-3-carboxamido)-α-phenylacetamido]-3-carbamoyloxymethyl-3-cephem-4-carboxylic acid and the non-toxic, pharmaceutically acceptable salts thereof, of claim 1.

6. 7-[D-α-(4-Hydroxy-1,5-naphthyridine-3-carboxamido)-α-(p-hydroxyphenyl)acetamido]-3-carbamoyloxymethyl-3-cephem-4-carboxylic acid and the non-toxic pharmaceutically acceptable salts thereof, of claim 1.

7. 7-[D-α-(4-Hydroxy-1,5-naphthyridine-3-carboxamido)-α-phenylacetamido]-3-carbamoyloxymethyl-3-cephem-4-carboxylic acid and the non-toxic, pharmaceutically acceptable salts thereof, of claim 1.

8. 7-[D-α-(4-Hydroxy-1,5-naphthyridine-3-carboxamido)-α-(m-aminophenyl)acetamido]-3-carbamoyloxymethyl-3-cephem-4-carboxylic acid and the non-toxic, pharmaceutically acceptable salts thereof, of claim 1.

9. 7-[D-α-(2-Methylthio-5,8-dihydro-5-oxopyrido[2,3-d]pyrimidine-6-carboxamido)-α-(p- hydroxyphenyl)-acetamido]-3-carbamoyloxymethyl-3-cephem-4-carboxylic acid and the non-toxic, pharmaceutically acceptable salts thereof, of claim 1.

10. 7-[D-α-(5,8-Dihydro-5H-8-oxopyrido[3,2-d]pyrimidine-7-carboxamido)-α-(p-hydroxyphenyl)acetamdio]-3-carbamoyloxymethyl-3-cephem-4-carboxylic acid and the non-toxic, pharmaceutically acceptable salts thereof, of claim 1.

11. 7-[D-α-(4-Hydroxy-1,5-naphthyridine-3-carboxamido)-α-(3-chloro-4-hydroxyphenyl)acetamido]-3-carbamoyloxymethyl-3-cephem-4-carboxylic acid and the non-toxic, pharmaceutically acceptable salts thereof, of claim 1.

12. The sodium salt of the acid of claim 6.

13. The potassium salt of the acid of claim 6.

14. The acid of claim 6.

15. A non-toxic, pharmaceutically acceptable salt of the acid of claim 6.

16. The sodium salt of the acid of claim 7.

17. The potassium salt of the acid of claim 7.

18. The acid of claim 7.

19. A non-toxic, pharmaceutically acceptable salt of the acid of claim 7.

20. An acid having the D configuration in the 7-side-chain and the formula

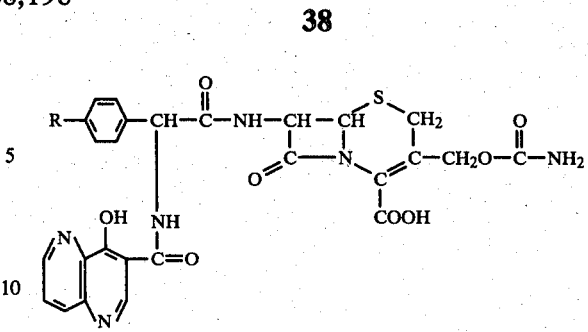

wherein R is hydrogen or hydroxy.

21. An acid having the D configuration in the 7-side-chain and the formula

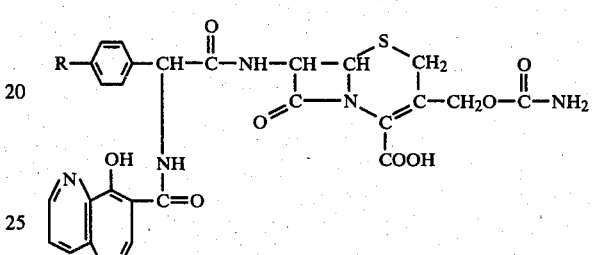

wherein R is hydrogen or hydroxy or a non-toxic, pharmaceutically acceptable salt of said acid.

22. The sodium salt of the acid of claim 21.

23. The potassium salt of the acid of claim 21.

24. A non-toxic, pharmaceutically acceptable salt of the acid of claim 21.

25. An antibacterial composition which comprises an antibacterially effective amount of a compound of claim 1 as an active ingredient and a pharmaceutically acceptable carrier or diluent.

* * * * *